US011806601B1

(12) United States Patent
Fowler (10) Patent No.: US 11,806,601 B1
(45) Date of Patent: Nov. 7, 2023

(54) BOWLER PERFORMANCE TRACKING SYSTEM

(71) Applicant: Suzanne Fowler, Jacksonville, FL (US)

(72) Inventor: Suzanne Fowler, Jacksonville, FL (US)

( * ) Notice: Subject to any disclaimer, the term of this patent is extended or adjusted under 35 U.S.C. 154(b) by 0 days.

(21) Appl. No.: 17/216,317

(22) Filed: Mar. 29, 2021

(51) Int. Cl.
  *A63B 71/06* (2006.01)
  *A63B 69/00* (2006.01)
  *A63B 24/00* (2006.01)

(52) U.S. Cl.
  CPC ...... *A63B 71/0622* (2013.01); *A63B 24/0021* (2013.01); *A63B 69/0046* (2013.01); *A63B 71/0669* (2013.01); *A63B 2024/0031* (2013.01); *A63B 2071/0661* (2013.01); *A63B 2220/30* (2013.01); *A63B 2220/62* (2013.01); *A63B 2220/803* (2013.01); *A63B 2220/806* (2013.01); *A63B 2220/807* (2013.01); *A63B 2220/836* (2013.01); *A63B 2225/50* (2013.01)

(58) Field of Classification Search
  CPC ............ A63B 71/0622; A63B 24/0021; A63B 69/0046; A63B 71/0669; A63B 2024/0031; A63B 2071/0661; A63B 2220/30; A63B 2220/62; A63B 2220/803; A63B 2220/806; A63B 2220/807; A63B 2220/836; A63B 2225/50
  See application file for complete search history.

(56) References Cited

U.S. PATENT DOCUMENTS

| 3,145,025 | A | 8/1964 | Morrison et al. |
| 5,118,105 | A | 6/1992 | Brim et al. |
| 6,032,530 | A | 3/2000 | Hock |
| 6,048,272 | A | 4/2000 | Tsujita |
| 6,110,052 | A | 8/2000 | Sprager et al. |
| 7,602,301 | B1 | 10/2009 | Stirling et al. |
| 7,837,571 | B2 * | 11/2010 | Romagnoli ............. A63D 5/04 473/53 |
| 7,930,131 | B2 | 4/2011 | Ridenour et al. |
| 7,978,081 | B2 | 7/2011 | Shears et al. |
| 8,040,758 | B1 | 10/2011 | Dickinson |
| 8,088,017 | B2 * | 1/2012 | Stremmel ............... A63D 5/04 473/109 |

(Continued)

OTHER PUBLICATIONS

"Apple Watch Bowling Activity Type" found at https://www.macrumors.com, Apr. 13, 2018.

*Primary Examiner* — Malina D. Blaise
(74) *Attorney, Agent, or Firm* — John Rizvi; John Rizvi, P.A.—The Patent Professor®

(57) ABSTRACT

A bowler performance tracking system monitors at least one of a number of steps in an approach, a maximum rearward angle attained by a bowling ball during the approach, a release angle of the bowling ball upon release by a bowler onto a bowling lane, a ball speed, an arm speed, a ball trajectory, and bowler scores during a bowling game. The system includes a wearable performance tracking device dimensioned and configured to be worn by the bowler and having a housing assembly with a motion sensor camera unit mounted therein. A digital display assembly is disposed on the housing assembly and is visible to the bowler. A control assembly includes a data storage unit configured to store an amount of data, and the control assembly also has a display interface operable with the digital display assembly to cause at least one display parameter to be displayed thereon.

11 Claims, 11 Drawing Sheets

(56) References Cited

U.S. PATENT DOCUMENTS

| | | | |
|---|---|---|---|
| 8,730,037 B2 | 5/2014 | Houvener et al. | |
| 9,568,492 B2 * | 2/2017 | Yuen | A61B 5/1123 |
| 9,814,426 B2 | 11/2017 | Connor | |
| 2009/0002316 A1 * | 1/2009 | Rofougaran | A63F 13/843 |
| | | | 345/156 |
| 2009/0011832 A1 * | 1/2009 | Rofougaran | H04M 1/72427 |
| | | | 463/41 |
| 2009/0143883 A1 * | 6/2009 | Pines | A63D 5/04 |
| | | | 434/249 |
| 2009/0270193 A1 * | 10/2009 | Stremmel | A63B 69/0046 |
| | | | 73/865.4 |
| 2014/0035226 A1 * | 2/2014 | Dayal | A63F 7/0608 |
| | | | 273/129 V |
| 2014/0094322 A1 * | 4/2014 | Rhodes | A63B 43/04 |
| | | | 473/126 |
| 2015/0122018 A1 * | 5/2015 | Yuen | A61B 5/4812 |
| | | | 73/514.01 |
| 2015/0127298 A1 * | 5/2015 | Gangumalla | A61B 5/1123 |
| | | | 702/160 |
| 2015/0374310 A1 * | 12/2015 | Lee | A61B 5/1118 |
| | | | 600/483 |
| 2020/0054928 A1 * | 2/2020 | Ananth | G16H 40/67 |

* cited by examiner

BOWLER PERFORMANCE TRACKING SYSTEM

FIELD OF THE INVENTION

The present invention relates generally to a bowler performance tracking system including a wearable performance tracking device.

BACKGROUND OF THE INVENTION

Although the number of persons who engage in the recreational sport of bowling is clearly not what it was during its heyday in the mid part of the previous century, 40 to 50 million Americans alone still take to the lanes each year in one of the thousands of bowling alleys which continue to operate across the country today. In addition, there are still thousands of "Pro Shops" which serve the various needs and whet the appetites of bowlers, from beginners to professionals, for all things bowling.

Despite the significant continued participation in the game, little has changed in the sport in the last century, especially in terms of embracing currently available technology. Of course, there was a shift to automatic pin spotters and automatic ball returns, and then came automatic scoring devices, along with motion detectors and alarms on the foul line, but otherwise, the sport of bowling remains pretty much as it had at the start of the previous century. More recently, in order to appeal to younger bowlers, some bowling alleys feature colored and/or flashing lights, often combined with contemporary music played over the facilities PA system, so as to provide a more interesting environment for younger generations of bowlers.

Conversely, other sporting activities have embraced technology as a means to instruct a user how to perform, and more importantly, how to improve their performance in a particular sport. As one example, all manner of devices exist to help a golfer visualize a course, monitor and analyze his or her swing and/or communication with a ball. A golfer can review his or her performance after a hole or after a round of golf to learn from mistakes and to take corrective actions in the future to improve his or her game.

Further, all manner of devices exist to monitor persons who walk, power walk, jog or ride to let him or her know how fast, how far, how long, etc. Stationary cycling units often include a video monitor with a virtual trainer displayed to rally and direct a user to achieve his or her particular cycling and/or exercise goals. Many other devices exist which include one or more sensors to allow a user to monitor one or more of his or her vital health parameters, such as heartrate, breathing rate, oxygen levels, caloric usage, etc., such as while working out in a gym or engaging in one of the aforementioned activities.

However, little to nothing has been done to utilize modern technology in a manner which will assist a bowlers, whether a beginner or a professional, to improve his or her game. In fact, about the only tool available to most bowlers is to request a printout of his or her score after a game to review for consistency, etc. As will be appreciated, simply reviewing the score of ones game after the fact offers little to no guidance to a bowler, once again, whether a beginner or a professional, as to what he or she did right, what he or she did wrong, or what he or she can do to improve their game.

Accordingly, there is an established need for a solution to one or more of the foregoing problems.

SUMMARY OF THE INVENTION

The present invention is directed generally to a bowler performance tracking system including a wearable performance tracking device.

In a first implementation of the invention, a bowler performance tracking system monitors one or more of a number of steps in an approach, a maximum rearward angle attained by a bowling ball during the approach, a release angle of the bowling ball upon release by a bowler onto a bowling lane, a ball speed, a ball trajectory, a frame score and a game score during a bowling game, and the system may comprise: a wearable performance tracking device dimensioned and configured to be worn by the bowler; the wearable performance tracking device having a housing assembly with a motion sensor camera unit mounted therein; a digital display assembly disposed on the housing assembly and visible to the bowler; and a control assembly disposed in the housing assembly having a data storage unit configured to store an amount of data thereon, the control assembly also having a display interface operable with the digital display assembly to cause at least one display parameter to be displayed thereon.

In a second aspect, the bowler performance tracking system can include an adjustable mounting unit to removably attach a wearable performance tracking device to a bowler.

In another aspect, the bowler performance tracking system may have a housing assembly comprising at least one data transfer port to transfer of an amount of data to or from a wearable performance tracking device via a physical connection.

In a further aspect, the bowler performance tracking system can include a housing assembly comprising at least one memory card port to transfer an amount of data to or from a wearable performance tracking device via a removable data memory card.

In one other aspect, the bowler performance tracking system may have a housing assembly comprising a face disposed on one surface thereof, and in one further embodiment, a digital display assembly is at least partially disposed on the face of the housing assembly.

In yet another aspect, the bowler performance tracking system can include a display interface operable with a digital display assembly to cause a plurality of display parameters to display thereon.

In still one further aspect, the bowler performance tracking system may have at least one display parameter comprising a time display.

In yet one other aspect, the bowler performance tracking system can include at least one display parameter comprising a score display.

In still another aspect, the bowler performance tracking system may have at least one display parameter comprising a ball speed display and/or an arm speed display.

In yet one further aspect, the bowler performance tracking system can include a display interface operable with a digital display assembly to display a data access button.

In still one other aspect, the bowler performance tracking system may have a display interface operable with a digital display assembly to display a data transfer button.

In yet another aspect, the bowler performance tracking system can include a display interface operable with a digital display assembly to display a power control button.

In still one further aspect, the bowler performance tracking system may have a display interface operable with a digital display assembly to display a wireless control button.

In yet one other aspect, the bowler performance tracking system can include a display interface operable with a digital display assembly to display a volume control button.

In still another aspect, the bowler performance tracking system monitors one or more of a number of steps in an approach, a maximum rearward angle attained by a bowling ball during the approach, a release angle of the bowling ball upon release by a bowler onto a bowling lane, a ball speed, a ball trajectory, a frame score and a game score during a bowling game, and the system may comprise: a wearable performance tracking device dimensioned and configured to be worn by the bowler; the wearable performance tracking device comprises a housing assembly having a housing unit including a face disposed on one side thereof; a motion sensor camera unit mounted to the housing unit and operable to track the ball speed and the ball trajectory of the bowling ball bowled by the bowler onto the bowling lane; a digital display assembly disposed on the face of the housing unit and visible to the bowler; a control assembly disposed in the housing assembly comprising a processor disposed in a communicative relation with a motion sensor camera unit interface operable with the motion sensor camera unit to cause the motion sensor camera unit to track at least the ball speed and the ball trajectory of the bowling ball bowled by the bowler on the bowling lane; the control assembly also having a data storage unit configured to store an amount of data thereon; and the control assembly further comprising a display interface operable with the digital display assembly to cause a plurality of display parameter to display thereon.

In yet one further aspect, the bowler performance tracking system can include a plurality of display parameters including at least one or more of a time display, a score display, a ball speed display, and an arm speed display.

In still one other aspect, the bowler performance tracking system may have a data transfer interface to facilitate a transfer of an amount of data to or from a wearable performance tracking device.

In yet another aspect, the bowler performance tracking system can include a wireless interface to facilitate wireless communications to or from the wearable performance tracking device.

In still one further aspect, the a bowler performance tracking system monitors one or more of a number of steps in an approach, a maximum rearward angle attained by a bowling ball during the approach, a release angle of the bowling ball upon release by a bowler onto a bowling lane, a ball speed, a ball trajectory, a frame score and a game score during a bowling game, and the system may comprise: a wearable performance tracking device dimensioned and configured to be worn by the bowler; the wearable performance tracking device comprising a housing assembly having a housing unit including a face disposed on one side and a base disposed on an opposite side thereof, the base comprising at least one device charging interface mounted thereto; a motion sensor camera unit mounted to the housing unit and operable to track the ball speed and the ball trajectory of the bowling ball bowled by the bowler onto the bowling lane; a digital display assembly disposed on the face of the housing unit and visible to the bowler; a control assembly disposed in the housing assembly comprising a processor disposed in a communicative relation with a motion sensor camera unit interface operable with the motion sensor camera unit to cause the motion sensor camera unit to track at least the ball speed and the ball trajectory of the bowling ball bowled by the bowler on the bowling lane; the control assembly further comprising a display interface operable with the digital display assembly to cause a plurality of display parameters to display thereon, the plurality of display parameters include at least one or more of a time display, a score display, and a ball speed display; and a charging assembly comprising a charging cradle dimensioned to receive a portion of the base of the wearable performance tracking device therein and having at least one charging cradle interface mounted thereto, the at least one device charging interface and the at least one charging cradle interface disposable into an electrically communicative orientation to provide an electrical charge from the charging assembly to a power supply of the wearable electronic device.

In yet another aspect, the bowler performance tracking system can include fitness tracking monitors to monitor a user's vital health statistics such as pedometric activity, blood pressure, blood oxygen level, pulse rate, respiration rate, and/or stress level.

In still one further aspect, the bowler performance tracking system may have an electroencephalograph including a conductive metal inserted into a silicone earbud worn by a user to track sleep performance data, among other parameters.

In yet one other aspect, the bowler performance tracking system can include access to music subscriptions and/or satellite music stations.

In still another aspect, the bowler performance tracking system may have access to audible books and/or e-books.

In yet one further aspect, the bowler performance tracking system can include access to weather monitoring services and/or may comprise a barometric pressure sensor to alert a user to potentially hazardous weather conditions.

In still one other aspect, the bowler performance tracking system may have access to the National Institute of Standards & Technology, for example, so as to allow the current time and date to be displayed via a display assembly.

In yet another aspect, the bowler performance tracking system can include a global positioning system receiver.

In yet another aspect, the bowler performance tracking system can include connectivity to a user's mobile cellular device so as to permit a user to send or receive text messages, emails, and conduct audio and video calls via a wearable performance tracking device.

In still one further aspect, the bowler performance tracking system may have a water resistant or water proof housing assembly.

In yet one other aspect, the bowler performance tracking system can include an external charging port and/or a power source having a 30 day charge capacity.

These and other objects, features, and advantages of the present invention will become more readily apparent from the attached drawings and the detailed description of the embodiments, which follow.

BRIEF DESCRIPTION OF THE DRAWINGS

The embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "top", "bottom", "left", "right", "front", "rear", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

As shown throughout the figures, in at least one embodiment, the present invention is directed to a bowler performance tracking system including a wearable performance tracking device.

Figure 1:
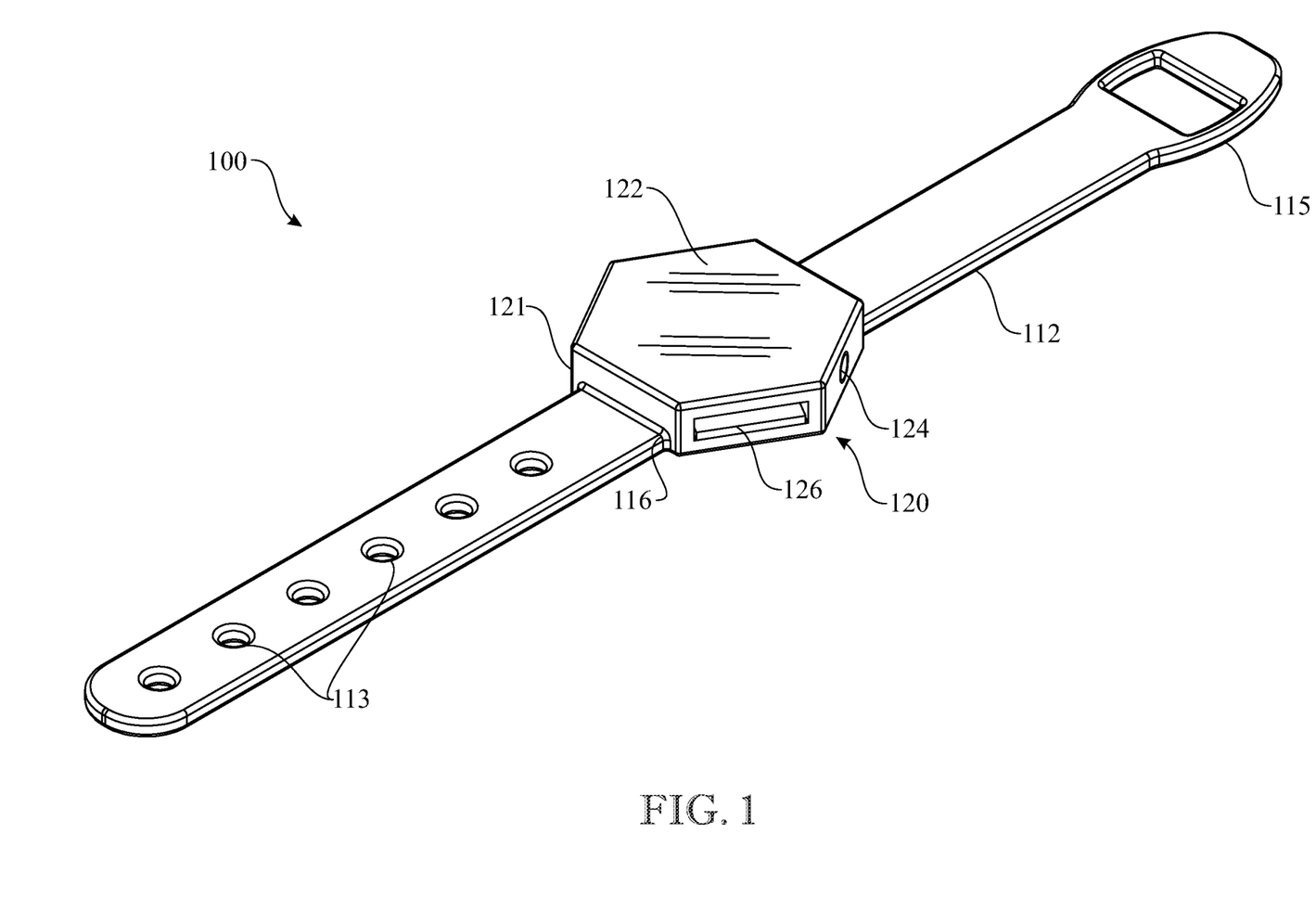
FIG. 1 presents a top perspective view of one illustrative embodiment of a bowler performance tracking system, in accordance with the present invention.
Figure 2:
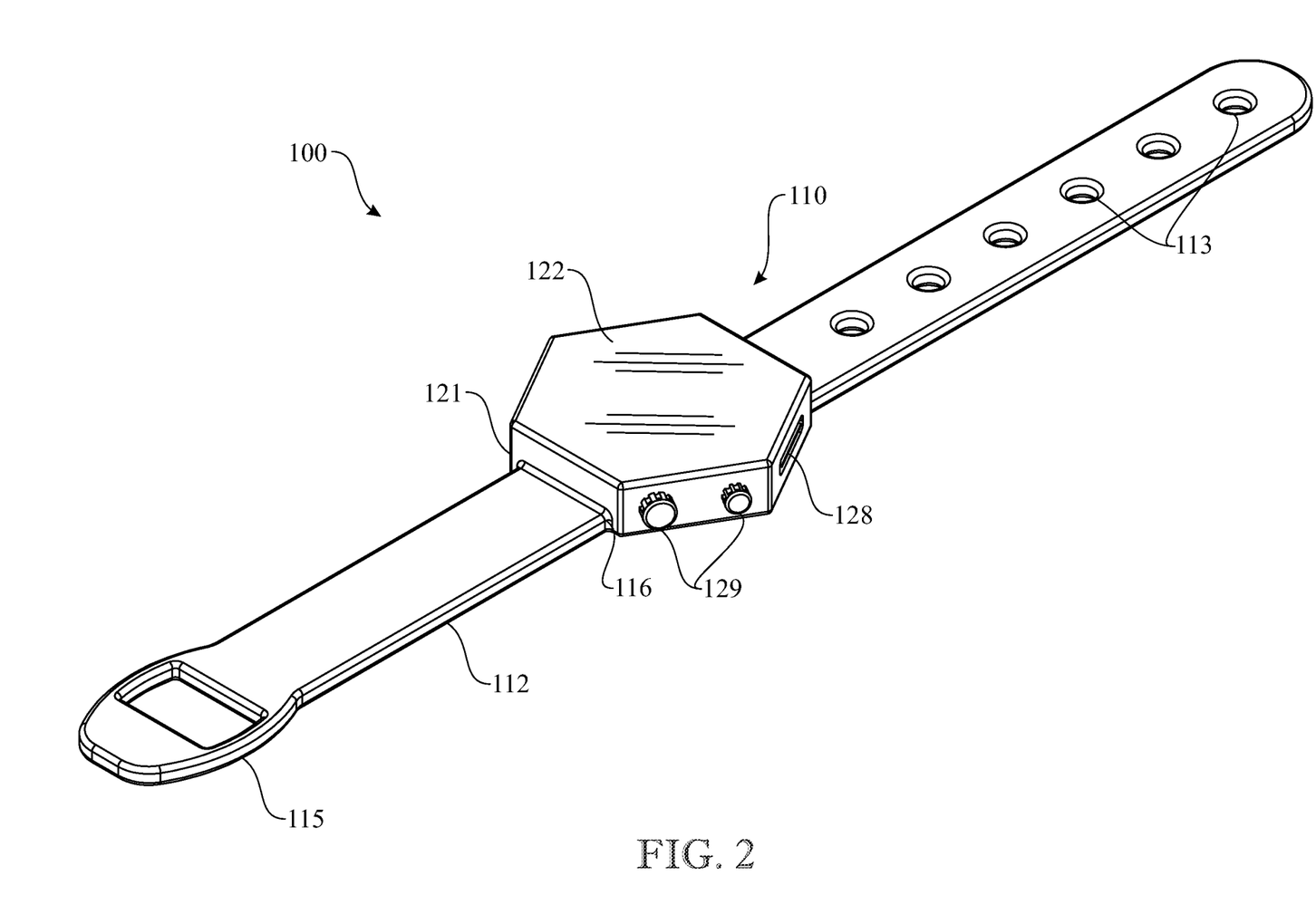
FIG. 2 presents another top perspective view of the bowler performance tracking system of FIG. 1, in accordance with the present invention.

Referring initially to FIGS. 1 and 2, perspective views of one illustrative embodiment of a bowler performance tracking system, generally as shown as at 100, are presented. As shown in the figures, a bowler performance tracking system 100 includes a wearable performance tracking device 110, which is dimensioned and configured to be worn by a bowler at least while he or she is engaged in a bowling game. In at least one embodiment, a wearable performance tracking device 110 includes a housing assembly 120.

Figure 3:
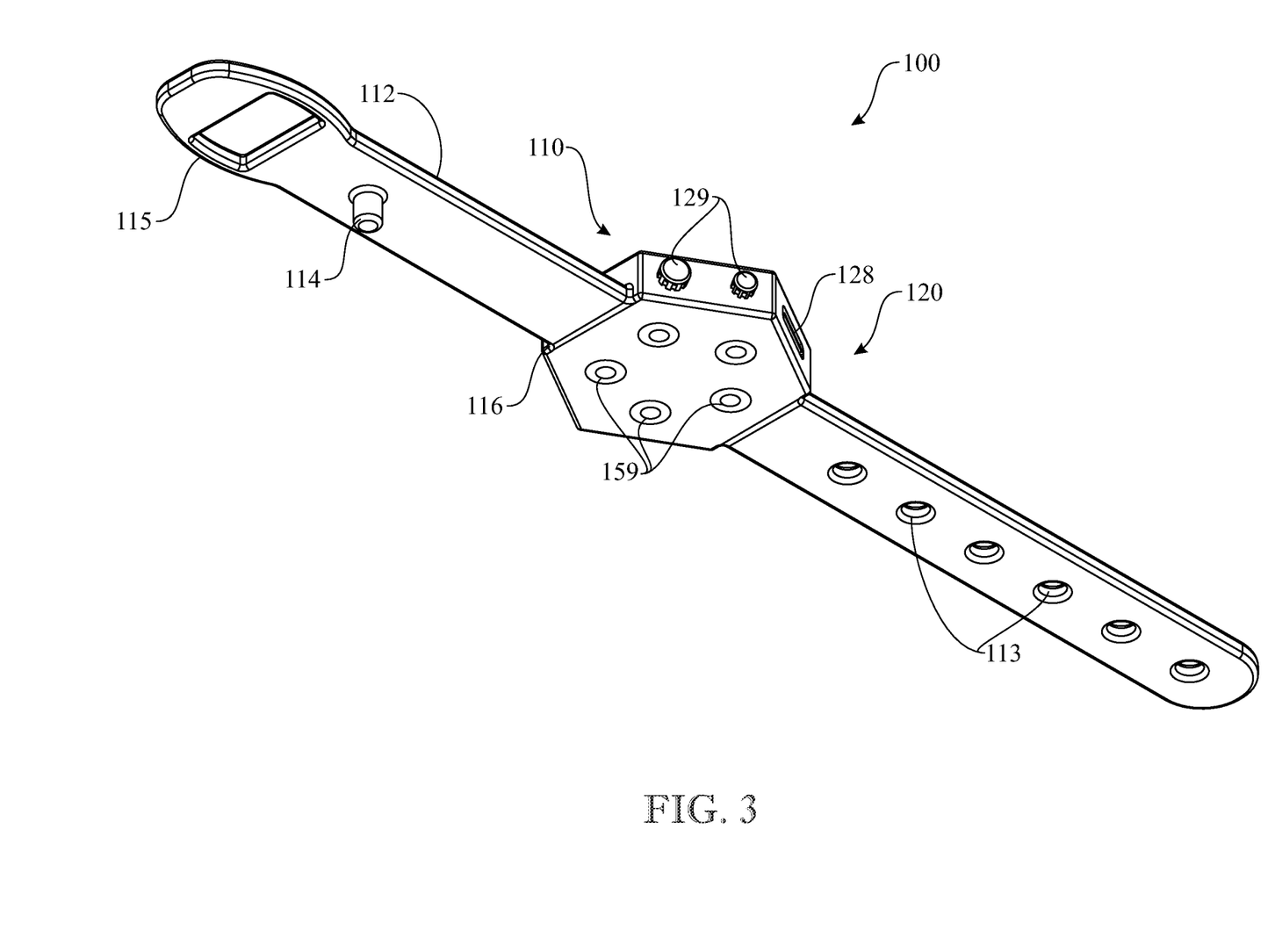
FIG. 3 presents a bottom perspective view of the bowler performance tracking system of FIG. 1, in accordance with the present invention.

With continued reference to FIGS. 1 and 2, an adjustable mounting unit 112 is provided to allow a bowler to quickly and easily attach the present wearable performance tracking device 110 about his or her wrist. In at least one embodiment, an adjustable mounting unit 112 may include one or more elongated strap or band like member attached to a housing assembly 120. In at least one embodiment, an adjustable mounting unit 112 is attached to a portion of a housing unit 121 of a housing assembly 120 via one or more attachment 116, such as is shown best in the illustrative embodiments of FIGS. 1 through 3.

An adjustable mounting unit 112 in accordance with at least one embodiment of the present invention comprises at least one mounting aperture 113. The mounting aperture 113 is dimensioned and configured to receive at least a portion of a mounting member 114 therethrough so as to releasably attach oppositely disposed elongated straps or band like members of an adjustable mounting unit 112 about a portion of a bowler's wrist. An adjustable mounting unit 112 can include a plurality of mounting apertures 113, such as is shown by way of example in the illustrated embodiments of FIGS. 1 through 3, wherein each of the plurality of mounting apertures 113 is dimensioned and configured to receive at least a portion of a mounting member 114 therethrough, so as to adjustably yet releasably attach the oppositely disposed elongated straps or band like members of the adjustable mounting unit 112 about a portion of a bowler's wrist. In at least one further embodiment, an adjustable mounting unit 112 includes a mounting member interconnect 115, such as, by way of example only, a buckle, a clip or a hasp, configured to receive and retain at least a portion of an elongated strap or band like a member therethrough while the adjustable mounting unit 112 is disposed about a portion of a bowler's wrist. It is to be appreciated that it is within the scope and intent of the present invention for an adjustable mounting unit 112 in accordance with the present invention may comprise a variety of other configurations than as shown throughout the figures.

A housing assembly 120 in accordance with the present invention comprises a face 122 disposed on one surface thereof and a base 123 disposed on an opposite surface. With reference once again to the illustrative embodiments of FIGS. 1 through 3, a face 122 is disposed on one surface of a housing unit 121 and a base 123 is disposed on the opposite surface of the housing unit 121.

Figure 6:
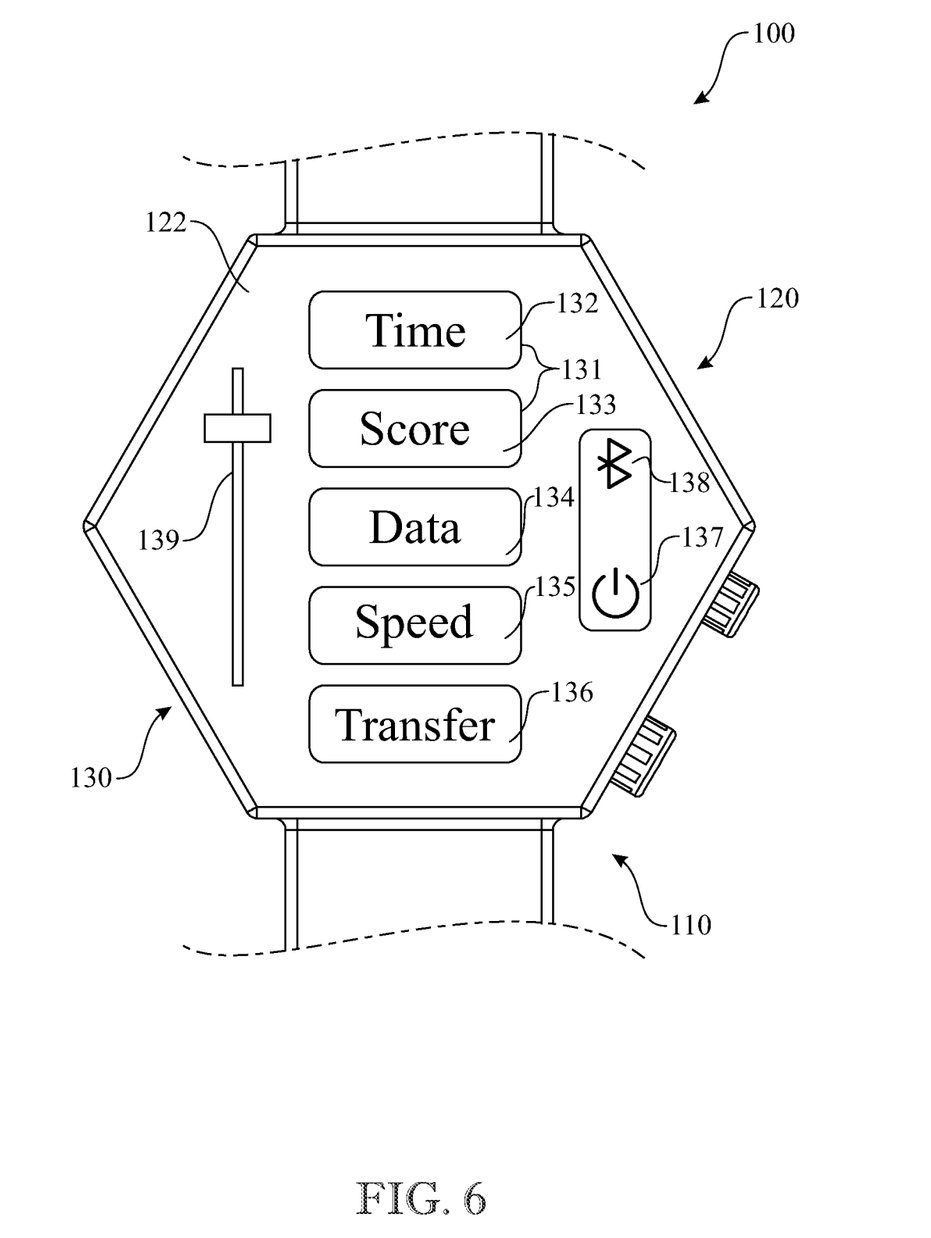
FIG. 6 presents a partial top plan view of one illustrative embodiment of a bowler performance tracking system showing one illustrative embodiment of a display assembly, in accordance with the present invention.

A wearable performance tracking device 110 in accordance with at least one embodiment of the present invention further comprises a display assembly 130. More in particular, a display assembly 130 is operable to display at least one display parameter 131 thereon, and is visible to and viewable by a bowler or other user to which the wearable performance tracking device 110 is attached. With reference to FIG. 6, a wearable performance tracking device 110 includes a display assembly 130 disposed at least partially on a face 122 of a housing unit 121 of a housing assembly 120.

As may be seen from FIG. 6, a plurality of display parameters 131 displayed by a display assembly 130 in accordance with at least one embodiment of the present invention include, but are in no manner limited to, a time display 132 which displays the current time and/or date in a time zone in which the wearable performance tracking device 110 is located and/or in various other user selected time zones, a score display 133 which displays a score of a current roll, a current frame and/or a current game, and a ball speed display 135 which displays an initial ball speed as a bowling ball is first released onto a bowling lane, a current or real time ball speed of the bowling ball as it travels down a bowling lane after release by a bowler, an average ball speed, a minimum ball speed, a maximum ball speed and/or an impact ball speed at the time of contact with one or more bowling pins by the bowling ball.

As further shown in FIG. 6, in at least one embodiment, a plurality of display parameters 131 displayed by a display assembly 130 include a plurality of buttons which facilitate operation of the present wearable performance tracking device 110 by a user. For example, a data access button 134 is provided to allow a user to access an amount of data stored in a data storage unit 143 of a control assembly 140, as discussed in greater detail below. Further, a display assembly 130 may include a data transfer button 136 to allow a user to download or upload an amount of data to or from the data storage unit 143, respectively.

As will be appreciated by those of skill in the art, a plurality of display parameters 131 visible on a display assembly 130 may include all or only some of the aforementioned plurality of display parameters 131, as well as additional display parameters 131, as discussed further hereinafter. As further shown in FIG. 6, the plurality of display parameters 131 may further include a power control button 137 operable to power up or turn off the present wearable performance tracking device 110, a wireless control button 138 operable to initiate formation of a wireless communication link between the wearable performance tracking device 110 and one or more remote devices, and a volume control button 139 operable to control a volume output from the wearable performance tracking device 110. In at least one further embodiment, a wearable performance tracking device 110 comprises one or more control knobs 129 which may be selectively configured to further facilitate operation of the device 110 by a user.

Figure 4:
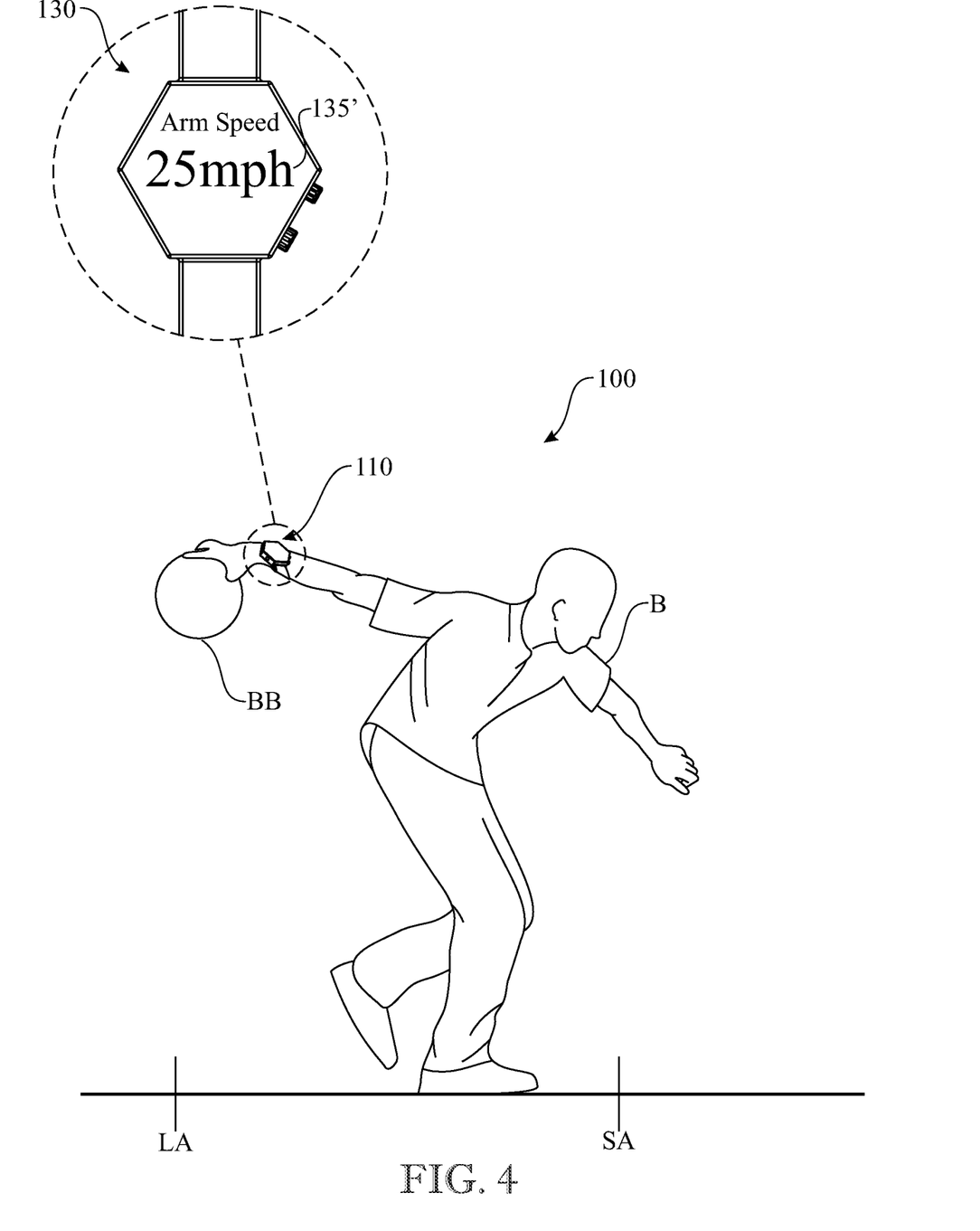
FIG. 4 presents a perspective view of the bowler performance tracking system of FIG. 1 showing a bowler with a bowling ball in motion, in accordance with the present invention.

A housing assembly 120 in accordance with at least one embodiment of the present wearable performance tracking device 110 further comprises a motion sensor camera unit 124 mounted thereto. A motion sensor camera unit 124, in at least one embodiment, comprises a motion sensor which functions as a pedometer operable to track a number of steps in an approach of a bowler up to a point of release of a bowling ball onto a bowling lane. With reference to the illustrative embodiment of FIG. 4, a bowler's approach may begin at a furthest distance from a foul line of a bowling lane, i.e., a long approach (LA), as represented in FIG. 4. Alternatively, a bowler's approach may begin at a closer distance to a foul line of a bowling lane, i.e., a short approach (SA), such as is also shown by way of example in FIG. 4. The present wearable performance tracking device 110 in at least one embodiment further comprises a control assembly 140 having a data storage module 143, discussed in greater detail hereinafter, disposed in communication with a motion sensor camera unit 124 for purposes of storing an amount of data indicative of a number of steps in each of a plurality of approaches by a bowler up to a point of release of a bowling ball onto a bowling lane for each roll, such as occurs during a bowling game.

A motion sensor camera unit 124, in one further embodiment, comprises a motion detector operable to track a maximum rearward angle attained by a bowling ball during an approach and/or a release angle of the bowling ball upon release by the bowler onto a bowling lane. In at least one embodiment, a motion detector of a motion sensor camera unit 124 is further operable to determine an arm speed of a bowler during an approach. With reference once again to FIG. 4, a display assembly 130 of a wearable performance tracking device 110 may be utilized to show an arm speed display 135' indicative of a current, average, maximum or minimum arm speed of a bowler (B) throughout an approach and release of a bowling ball (BB) onto a bowling lane. As before, in at least one embodiment, the present wearable performance tracking device 110 comprises a control assembly 140 including a data storage module 143 disposed in communication with a motion sensor camera unit 124 for purposes of storing an amount of data indicative of a plurality of maximum rearward angles attained by a bowling ball during an approach and a corresponding plurality of release angles of the bowling ball upon release by the bowler onto a bowling lane and/or a current, average, maximum and/or minimum arm speed of a bowler, such as occurs during a bowling game.

In another embodiment, a motion sensor camera unit 124 is operable to track a ball speed of a bowling ball bowled by the bowler onto a bowling lane. More in particular, a motion sensor camera unit 124 in accordance with at least one embodiment of the present invention is equipped with a break speed radar detector, somewhat similar to those employed in baseball to measure a speed of the ball released by a pitcher, as well as those used by law enforcement to measure the speed of vehicles travelling along roadways. As will be appreciated, a radar detector can detect an initial ball speed as a bowling ball is first released onto a bowling lane, a current or real time ball speed of the bowling ball as it travels down a bowling lane after release by a bowler, an average ball speed, a minimum ball speed, a maximum ball speed and/or an impact ball speed at the time of contact with one or more bowling pins by the bowling ball. Once again, the present wearable performance tracking device 110 has a control assembly 140 disposed in communication with a data storage module 143 for purposes of storing an amount of data indicative of a plurality of ball speeds of a bowling ball bowled by a bowler onto bowling lane during multiple frames, as measured by the motion sensor camera unit 124 in accordance with the present invention.

In at least one further embodiment, a motion sensor camera unit 124 comprises a motion detector operable to track a ball trajectory of a bowling ball bowled by a bowler onto a bowling lane. As such, a motion sensor camera unit 124 includes a camera having a lens configured to follow movement of a bowling ball down a bowling lane based on the trajectory of the bowling ball detected by the motion detector. Specifically, in at least one embodiment, a motion sensor camera unit 124 comprises a camera with a lens configured to pan across the width of a bowling lane in order to maintain focus on a bowling ball traveling down the bowling lane. In one embodiment, a motion sensor camera unit 124 includes a camera with a lens configured to cause the lens to pan right (PR), pan left (PR), or focus straight ahead (FS), once again, based on the trajectory of the bowling ball detected by the motion detector. In yet one further embodiment, a motion sensor camera unit 124 includes a camera with a lens having a sensor configured to cause the lens to pan right (PR), pan center right (PCR), focus straight (FS), pan center left (PCL) or pan left (PL), as before, based on the trajectory of the bowling ball detected by the motion detector.

As one example, a right handed bowler most often releases a bowling ball on the right side of the bowling lane directed toward the 1, 3, 5, 9 pin pocket on a first roll in a frame. In such a case, the motion detector will track the trajectory of the bowling ball and will cause the lens of the camera of the motion sensor camera unit 124 to pan center left (PCL) in order to capture the travel of the bowling ball down the bowling lane and to record the result of the roll. Similarly, a left handed bowler most often releases a bowling ball on the left side of the bowling lane directed toward the 1, 2, 4, 8 pin pocket on a first roll in a frame, in which case, the motion detector will track the trajectory of the bowling ball and will cause the lens of the camera of the motion sensor camera unit 124 to pan center right (PCR), once again, in order to capture the travel of the bowling ball down the bowling lane and to record the result of the roll.

As will be appreciated, in some instances, a bowler rolls the bowling ball straight at a particular pin, in which case, the motion detector will track the trajectory of the bowling ball and will cause the lens of the camera of the motion sensor camera unit 124 to focus straight (FS). Alternatively, in the event a bowler leaves a split, e.g., a 7-10 split, the motion detector will track the trajectory of the bowling ball and will cause the lens of the camera of the motion sensor camera unit 124 to pan left (PL) or pan right (PR), depending on which side the bowler releases the bowling ball onto the bowling lane, once again, in order to capture the travel of the bowling ball down the bowling lane and to record the result of the roll.

Figure 5:
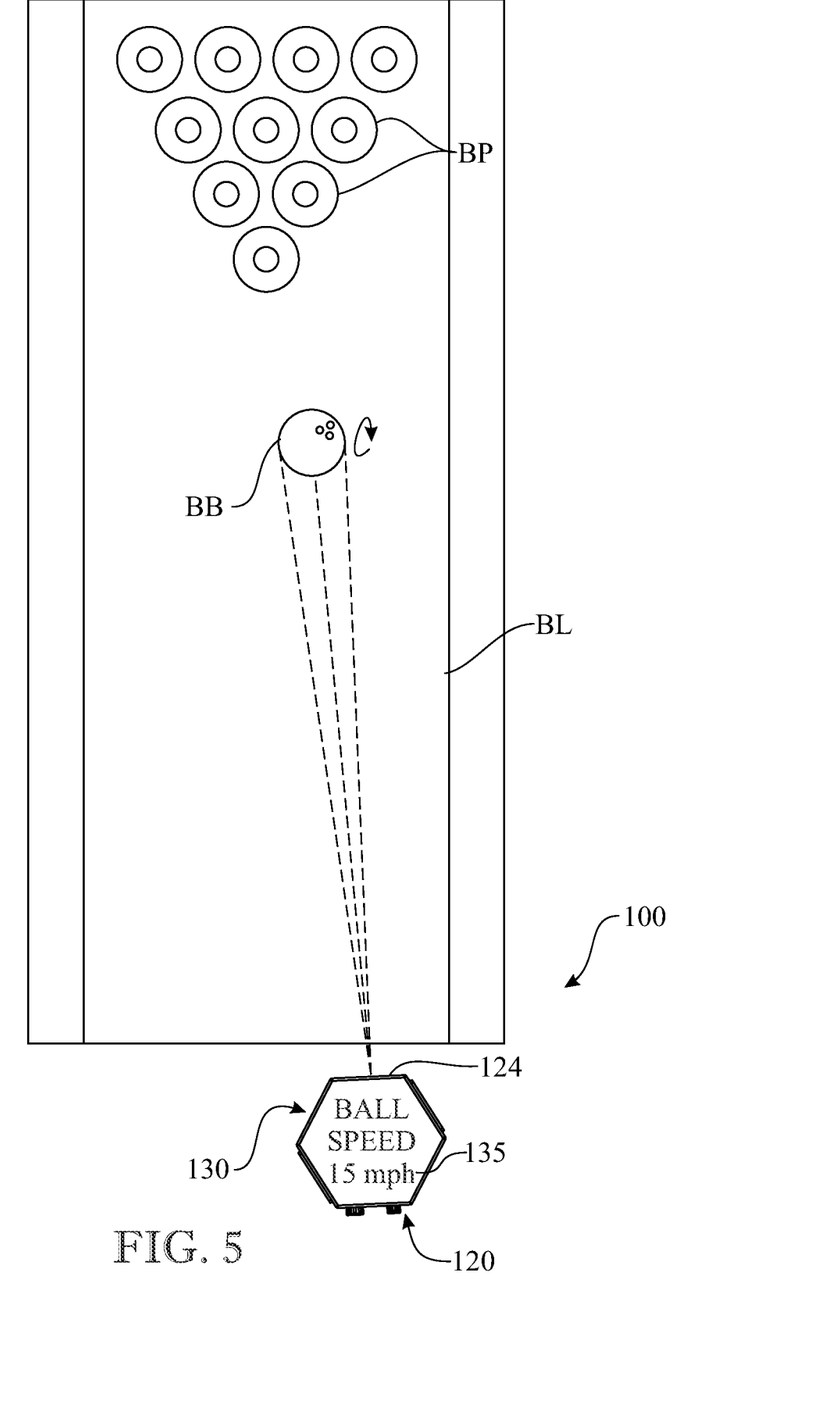
FIG. 5 presents a diagrammatic view of one illustrative embodiment of a bowler performance tracking system tracking a bowling ball travelling down a bowling lane, in accordance with the present invention.

As such, no matter where a bowling ball travels across a length or width of a bowling lane, the motion sensor camera unit 124 in accordance with the present invention is capable of following the movement of the bowling ball across the entire length and width of the bowling lane, such as is shown by way of example in the illustrative embodiment of FIG. 5. As before, in at least one embodiment the present wearable performance tracking device 110 comprises a control assembly 140 having a data storage module 143 disposed in communication with a motion sensor camera unit 124 for purposes of storing an amount of data indicative of a plurality of ball trajectories of a bowling ball bowled by the bowler onto bowling lane, such as occurs during a bowling game.

By virtue of monitoring and recording a ball speed and ball trajectory of a bowling ball across the entire width and length of a bowling lane, the present motion sensor camera unit 124 likewise visually records the outcome of each roll of each frame of each bowling game. As such, in combination with a processor 142 of the control assembly 140, the present bowler performance tracking system 100 is operable to calculate a score for each roll of each frame of each game bowled by the bowler wearing the present wearable performance tracking device 110, and to generate a corresponding score display 133 therefrom, as discussed in more detail below. In at least one further embodiment, a control assembly 140 having a data storage module 143 is disposed in communication with a motion sensor camera unit 124 for purposes of storing a video recording of each of a plurality of rolls of a bowling ball bowled by the bowler onto bowling lane.

As well be appreciated by those of skill in the art, a wearable performance tracking device 110 of the present bowler performance tracking system 100, and in particular, a wearable performance tracking device 110 having a motion sensor camera unit 124 in combination with a processor 142 and a data storage module 143 of the control assembly 140 thereof, permits the collection, storage, and analysis of all of the critical parameters of a bowler's performance throughout the bowling game including, at least, a number of steps in an approach, a maximum rearward angle attained by a bowling ball during the approach, a release angle of the bowling ball upon release by the bowler onto a bowling lane, an arm speed, a ball speed, a ball trajectory, a roll score, a frame score and a game score during a bowling game, including strikes, spares, splits, split conversions, and errors. With this data, a bowler may analyze each and every aspect of his or her game, make adjustments, and directly measure the impacts thereof in real time utilizing the present wearable performance tracking device 110, in order to improve the overall performance of the bowler's game.

A wearable performance tracking device 110 in accordance with at least one embodiment of the present invention, as previously indicated, further comprises a control assembly 140. A control assembly 140 in one embodiment includes a processor 142, such as are known in the art for controlling the operation of small electronic devices as well as for managing data associated therewith. In at least one embodiment, a control assembly 140 includes a power source 141 which provides power to at least a processor 142 and a display assembly 130 of the present wearable performance tracking device 110.

Figure 9:
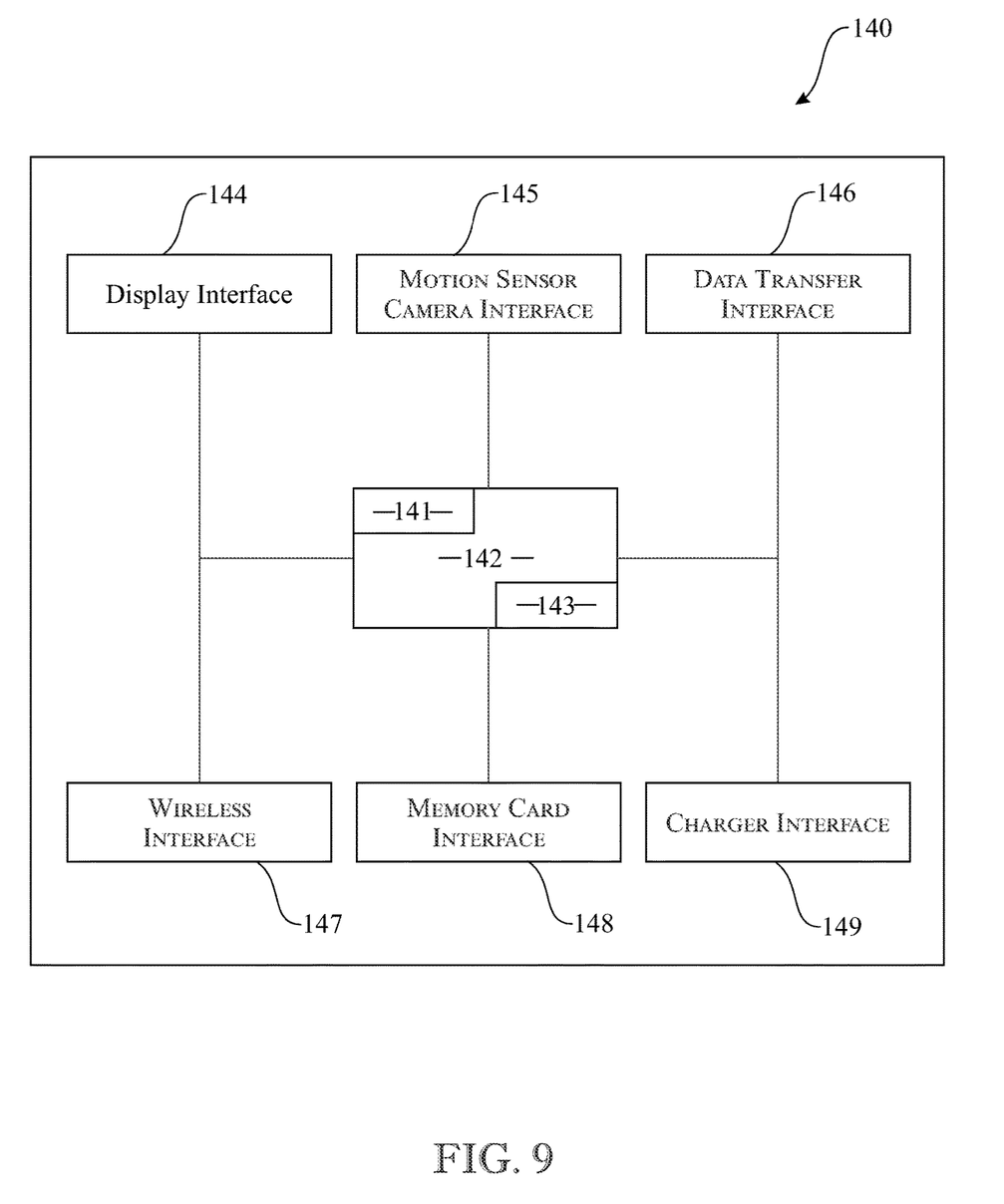
FIG. 9 presents a block diagram of one illustrative embodiment of a control assembly of a bowler performance tracking system, in accordance with the present invention.

In at least one embodiment, a control assembly 140 includes a plurality of interfaces operable with a processor in order to control the operation of various hardware components of a wearable performance tracking device 110 of the present bowler performance tracking system 100. With reference to FIG. 9, a control assembly 140 includes a display interface 144 operable with a display assembly 130. More in particular, a display interface 144 is disposed in communication between a processor 142 and a display assembly 130 and causes the display assembly 130 to display one or more of a plurality of display parameters 131 thereon, such as disclosed hereinabove.

In at least one further embodiment, and once again as shown in FIG. 9, a control assembly 140 comprises a motion sensor camera interface 145. A motion sensor camera interface 145 is disposed in communication between a processor 142 and a motion sensor camera unit 124. The motion sensor camera interface 145 receives a plurality of signals from a motion sensor camera unit 124 including at least signals from a motion sensor which the processor 142 is configured to translate into data indicative of a number of steps in an approach of a bowler up to a point of release of a bowling ball onto a bowling lane. The motion sensor camera interface 145 is further disposed in communication with a data storage unit 143, again, such as are known for use in portable electronic devices, and more importantly, the motion sensor camera interface 145 is operative to cause the data indicative of a number of steps in an approach of a bowler up to a point of release of a bowling ball onto a bowling lane to be stored onto the data storage unit 143, for subsequent retrieval and analysis by the processor 142, or by a remote computing device, a portable electronic device, and/or directly by a user.

In yet one further embodiment, a motion sensor camera interface 145 receives a plurality of signals from a motion sensor camera unit 124 including at least signals from a motion detector which the processor 142 is configured to translate into data indicative of a maximum rearward angle attained by a bowling ball during an approach and/or a release angle of the bowling ball upon release by the bowler onto a bowling lane. As before, the motion sensor camera interface 145 is operative to cause the data indicative of a maximum rearward angle attained by a bowling ball during an approach and/or a release angle of the bowling ball upon release by the bowler onto a bowling lane to be stored onto the data storage unit 143, for subsequent retrieval and analysis by the processor 142, or by a remote computing device, a portable electronic device, and/or directly by a user.

In at least one other embodiment, a motion sensor camera interface 145 receives a plurality of signals from a motion sensor camera unit 124 including at least signals from a radar detector which the processor 142 is configured to translate into data indicative of an initial ball speed as a bowling ball is first released onto a bowling lane, a current or real time ball speed of the bowling ball as it travels down a bowling lane after release by a bowler, an average ball speed, a minimum ball speed, a maximum ball speed and/or an impact ball speed at the time of contact with one or more bowling pins by the bowling ball. Once again, the motion sensor camera interface 145 is operative to cause the data indicative of an initial ball speed as a bowling ball is first released onto a bowling lane, a current or real time ball speed of the bowling ball as it travels down a bowling lane after release by a bowler, an average ball speed, a minimum ball speed, a maximum ball speed and/or an impact ball speed to be stored onto the data storage unit 143, for subsequent retrieval and analysis by the processor 142, or by a remote computing device, a portable electronic device, and/or directly by a user.

A further embodiment of a motion sensor camera interface 145 receives a plurality of signals from a motion sensor camera unit 124 including at least signals from a motion detector which the processor 142 is configured to translate into data indicative a ball trajectory of a bowling ball bowled by a bowler onto a bowling lane. In such an embodiment, a motion sensor camera interface 145 is further operable to transmit signals from the processor 142 to the motion sensor camera unit 124 to cause a lens of the motion sensor camera unit 124 to follow movement of a bowling ball down a bowling lane based on the trajectory of the bowling ball detected by the motion detector. As before, the motion sensor camera interface 145 is operative to cause the data indicative of a trajectory of a bowling ball from the moment is it is first released onto a bowling lane until impact with one or more bowling pins or entry into either gutter to be stored onto the data storage unit 143, for subsequent retrieval and analysis by the processor 142, or by a remote computing device, a portable electronic device, and/or directly by a user. In at least one further embodiment, a motion sensor camera interface 145, in at least one embodiment, is operative to cause video recordings and/or still images of a bowling ball captured by the motion sensor camera unit 124 from the moment is it is first released onto a bowling lane until impact with one or more bowling pins or entry into either gutter to be stored onto the data storage unit 143, for subsequent retrieval and analysis by the processor 142, or by a remote computing device, a portable electronic device, and/or directly by a user. The video recordings and/or still images captured by a motion sensor camera unit 124 may be utilized by the processor 142 to determine a score for each roll of each frame of each bowling game, and also as before, to store the scores onto the data storage unit 143, for subsequent retrieval and analysis by the processor 142, or by a remote computing device, a portable electronic device, and/or directly by a user.

Figure 7:
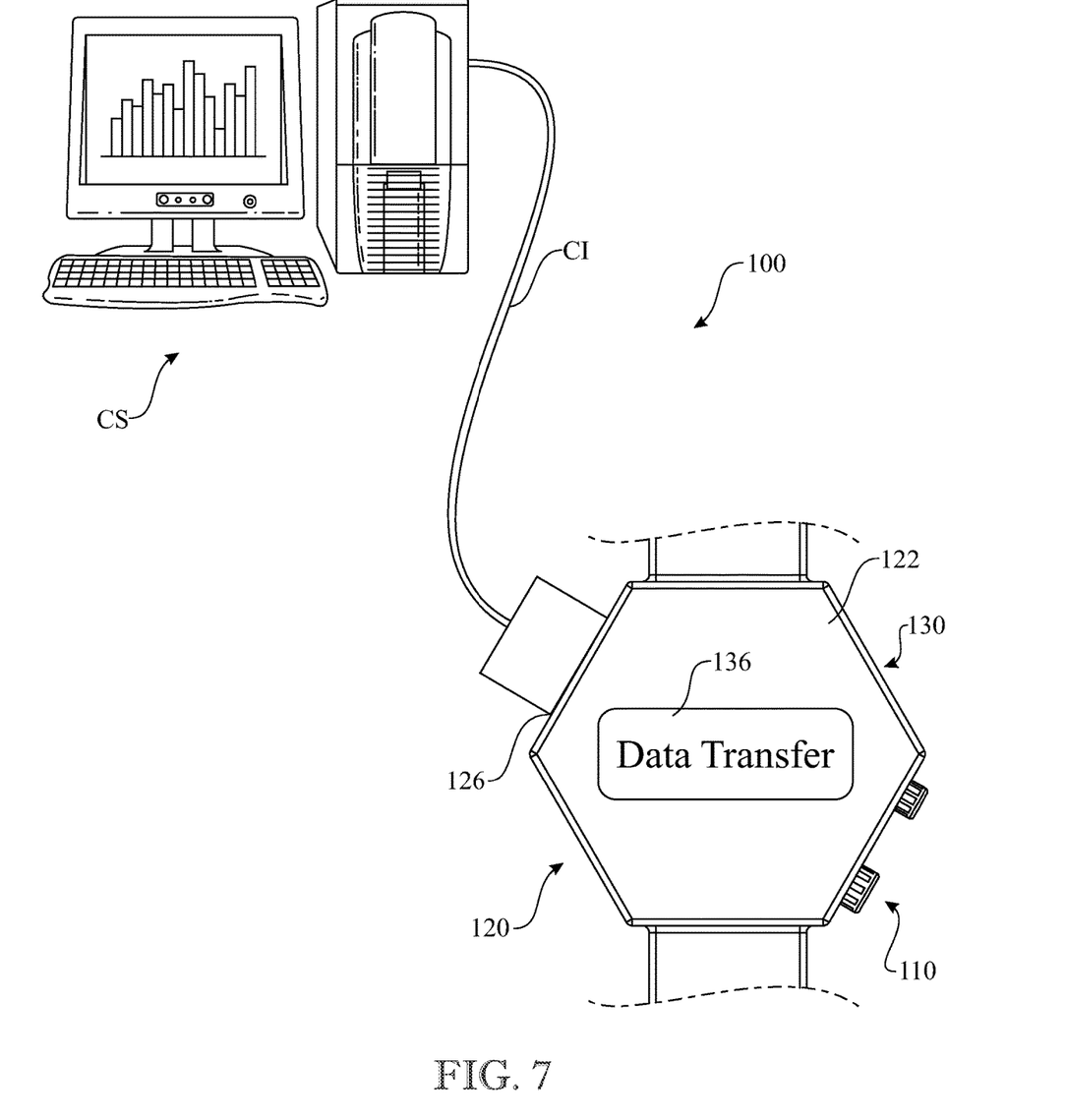
FIG. 7 presents a diagrammatic view of one illustrative embodiment of a bowler performance tracking system disposed in communication with a computer system, in accordance with the present invention.

A control assembly 140 in one embodiment of the present invention further comprises a data transfer interface 146 with is disposed in communication with a data transfer port 126 accessible on the wearable performance tracking device 110, as seen best in FIGS. 1 and 7. In at least one embodiment, a data transfer port comprises a universal serial bus or USB port, however, it is understood to be within the scope and intent of the present invention for the data transfer port 126 to comprise any of a variety of other ports capable of transferring data between electronic devices such as, by way of example only, a lightning connector port or an HDMI port. As further shown in FIG. 7, a computer interconnect (CI) is utilized to provide a physical connection between the data transfer port 126 of the wearable performance tracking device 110 and a computer system (CS) to facilitate uploading data from the computer system, such as, by way of example only, firmware updates or historical performance data from one or more users, to the wearable performance tracking device 110, and more in particular, to the data storage unit 143 for subsequent use by a processor 142. Further, a computer interconnect (CI) may be utilized to transfer an amount of data from a data storage unit 143 of a wearable performance tracking device 110 including performance data from one or more users for subsequent processing and analysis on the computer system (CS) and/or to physically print out for analysis by a user.

Figure 8:
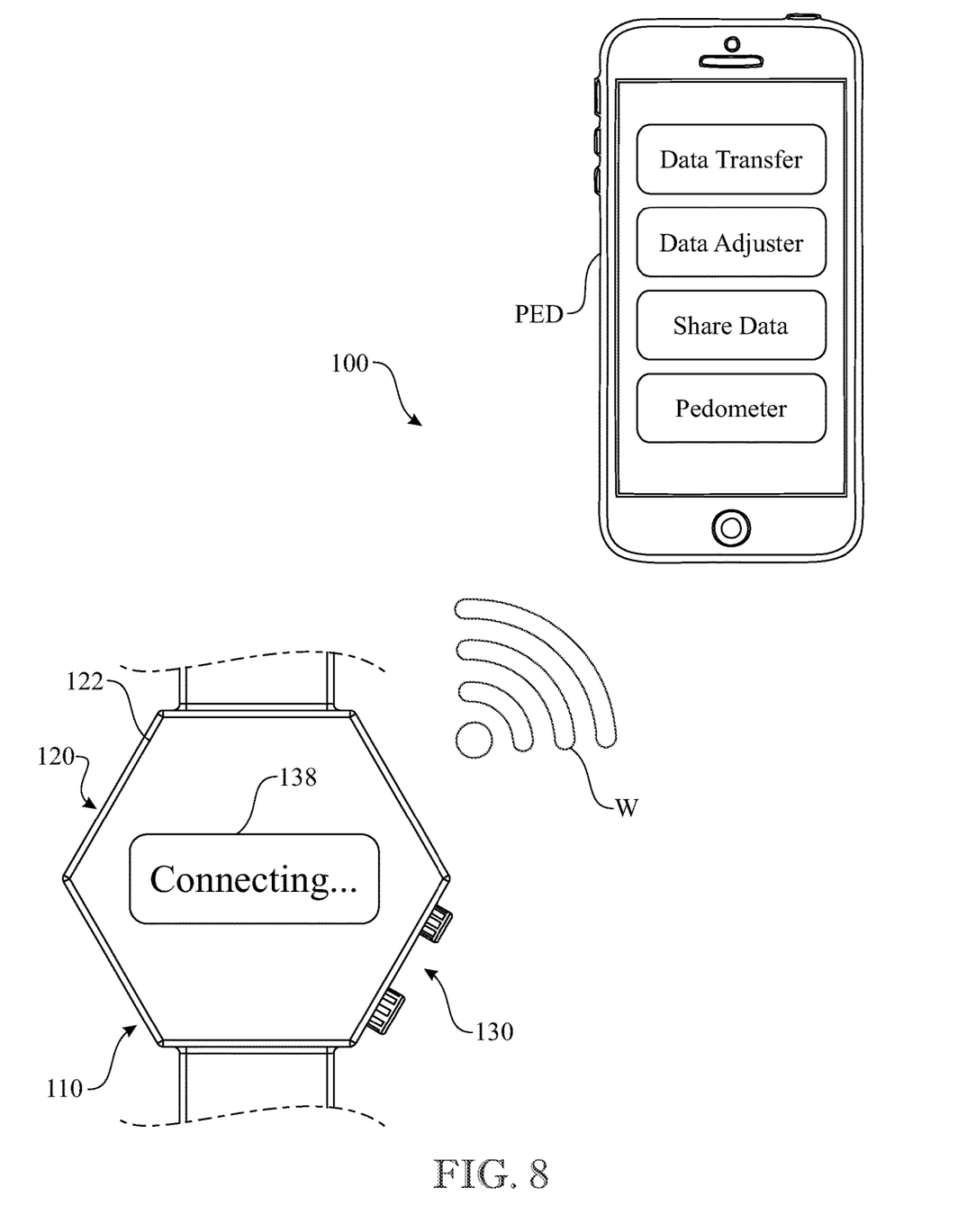
FIG. 8 presents a diagrammatic view of one illustrative embodiment of a bowler performance tracking system disposed in communication with a personal electronic device, in accordance with the present invention.

A control assembly 140 in at least one other embodiment of the present invention further comprises a wireless interface 147 with is disposed in communication with the processor 142 and the data storage unit 143. The wireless interface 147 is operable to create a wireless connection (W) between the present wearable performance tracking device 110 and a portable electronic device (PED), and to permit at least an amount of data to upload to or download from a portable electronic device (PED) via a wireless connection (W), as shown best in FIG. 8. In yet one further embodiment, a control assembly 140 comprises a memory card interface 148 disposed in communication between a processor and a memory card port 128, such as is shown best in FIGS. 2 and 3. As such, an amount of data may be uploaded to or downloaded from the wearable performance tracking device 110, and more in particular, to or from a data storage unit 143 thereof, for the purposes described hereinabove.

With reference again to FIG. 9, in at least one embodiment, a control assembly 140 further comprises a charger interface 149. A charger interface 149 is communicative with a power source 141 of a wearable performance tracking device 110, and more in particular, between a power source 141 disposed in a charging orientation on a charging assembly 150, as is described below, to facilitate electronic charging the power source 141.

In accordance with at least one embodiment, a bowler performance tracking system 100 in accordance with the present invention further comprises a charging assembly 150. More in particular, a charging assembly 150 is operable with one or more wearable performance tracking device 110 in order to impart an electronic charge to a power source 141 thereof.

Figure 10:
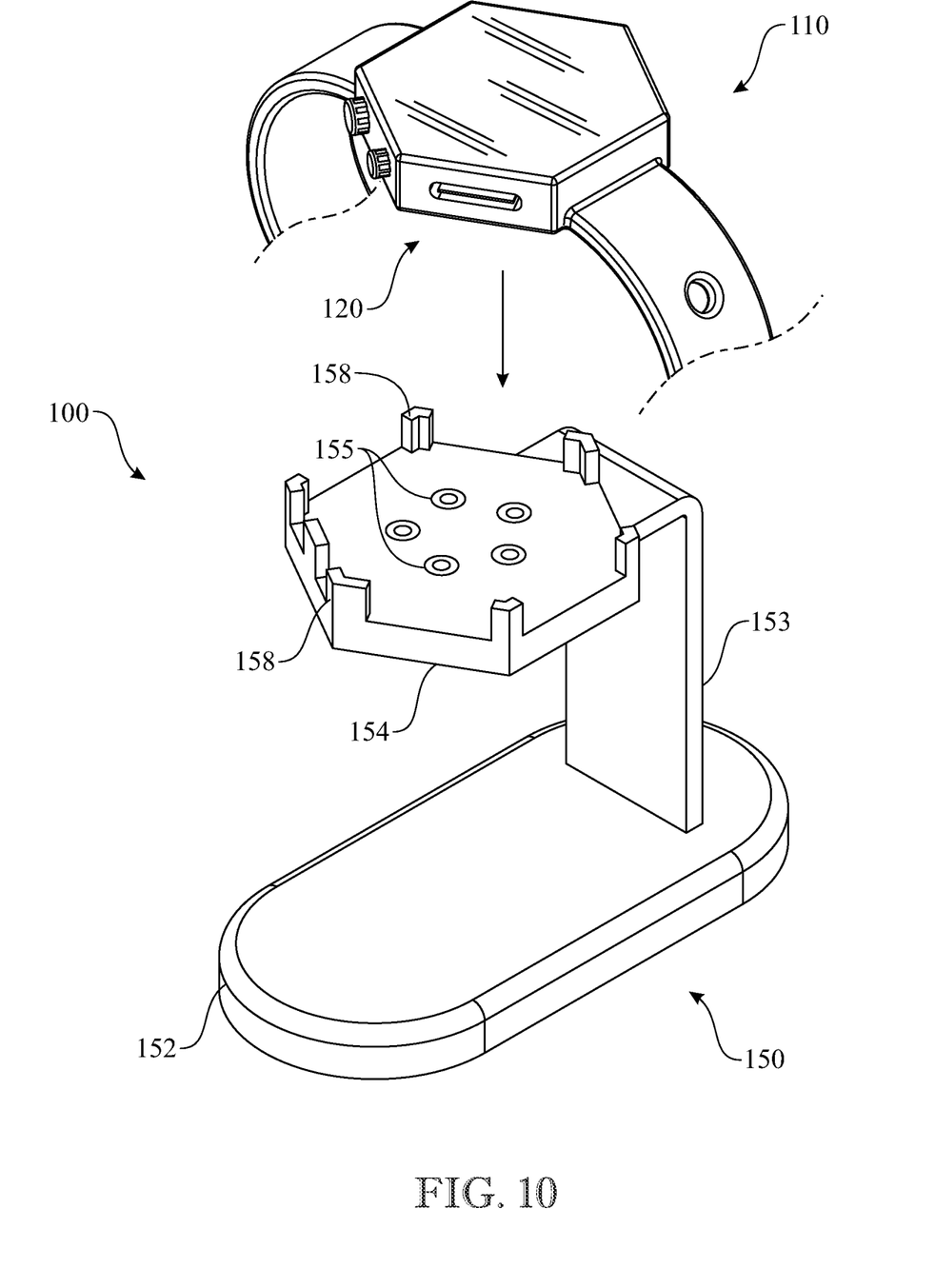
FIG. 10 presents a perspective view of one illustrative embodiment of a bowler performance tracking system including a charging assembly, in accordance with the present invention.
Figure 11:
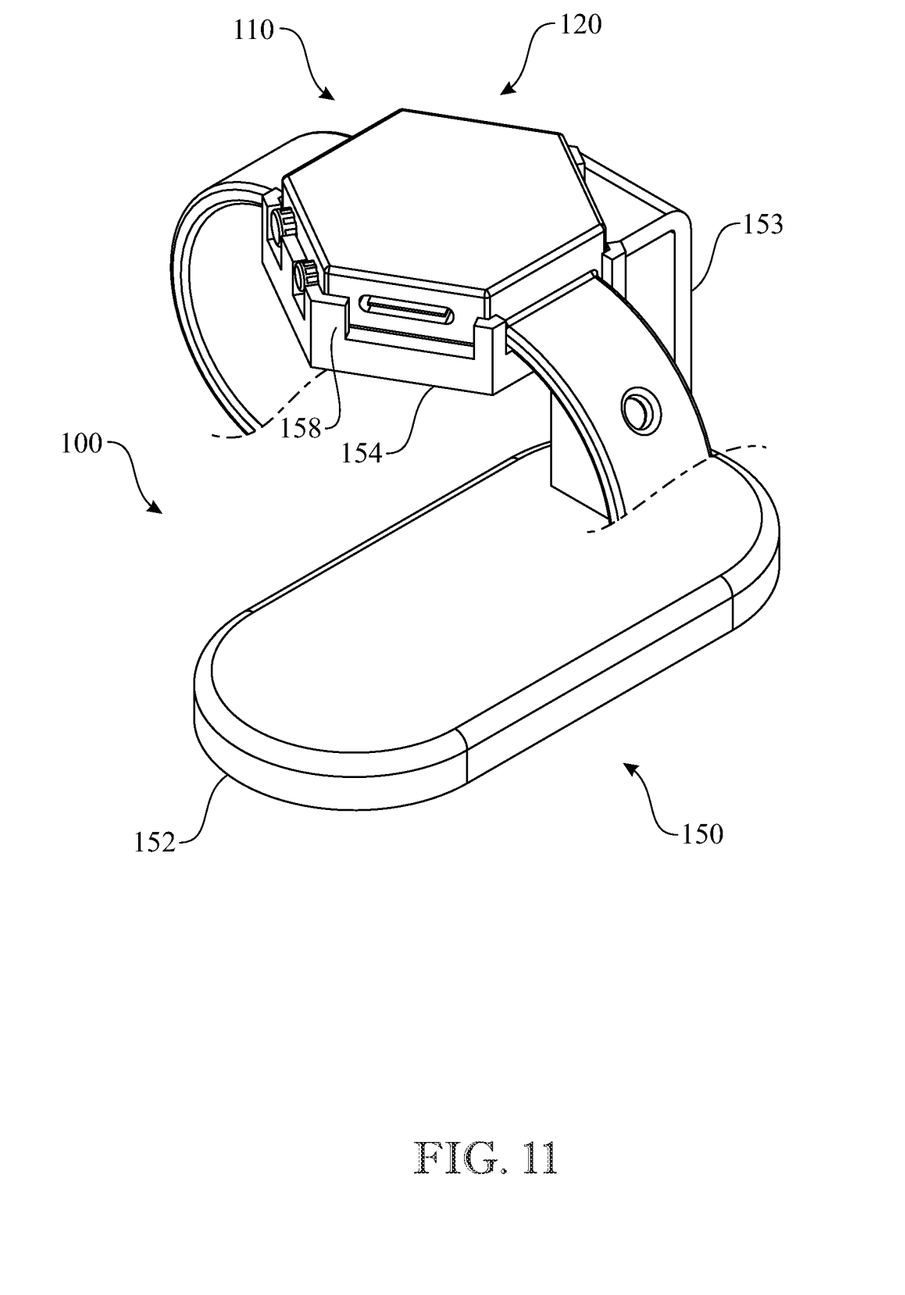
FIG. 11 presents a perspective view of the bowler performance tracking system of FIG. 10 showing a wearable performance tracking device disposed in a charging relation with the charging assembly, in accordance with the present invention.

With reference to the illustrative embodiment of FIGS. 10 and 11, a charging assembly 150 in accordance with the present invention comprises a base 152. In at least one embodiment, a base 152 may house one or more batteries which serve as a source of an electrical charge to be provided to a wearable performance tracking device 110. In at least one further embodiment, a charging assembly 150 is electrically connected to an external power source, such as, by way of example, a household electrical outlet.

With continued reference to FIGS. 10 and 11, in one embodiment, a charging assembly 150 includes a support arm 153 mounted at one end to the base 152, and interconnected to a charging cradle 154 at an opposite end. As may be seen from the figures, a charging cradle 154 in accordance with one embodiment of the present invention is dimensioned and configured to receive at least a portion of a housing assembly 120 of a wearable performance tracking device 110 therein during a charging operation. A charging assembly 150 may include at least one device support 158 configured and disposed to maintain a housing assembly 120 of a wearable performance tracking device 110 in position on a charging cradle 154 during a charging operation. As shown in the illustrative embodiment of FIG. 10, a charging assembly 150 in accordance with one embodiment of the present invention includes a plurality of device supports 158, each configured and disposed to maintain a housing assembly 120 of a wearable performance tracking device 110 in position on a charging cradle 154 during a charging operation.

A charging assembly 150 in accordance with one embodiment of the present invention further comprises at least one charging cradle interface 155 mounted thereto. More in particular, a charging assembly 150 includes at least one charging cradle interface 155 mounted to a portion of a charging cradle 154 and positioned to be disposable into an electrically communicative orientation relative to at least one device charging interface 129 disposed on a base 123 of a housing unit 121 of a wearable performance tracking device 110. In at least one further embodiment, such as is shown by way of example in FIG. 10, a charging assembly 150 includes a plurality of charging cradle interfaces 155 mounted to a portion of a charging cradle 154, each positioned to be disposable into an electrically communicative orientation relative to at least one device charging interface 129 disposed on a base 123 of a housing unit 121 of a wearable performance tracking device 110. As shown best in FIG. 3, in at least one embodiment, a wearable performance tracking device 110 includes a plurality of device charging interfaces 159 mounted to a base 123 of a housing unit 121 thereof. In one further embodiment, each of a plurality of device charging interfaces 159 is disposable into an electrically communicative orientation with a corresponding one of a plurality of charging cradle interfaces 155 to provide an electrical charge from the charging assembly 150 to a power supply 141 of a wearable performance tracking device 110 while the wearable performance tracking device 110 is disposed in a charging orientation with the charging assembly 150, as best seen in FIG. 11.

Since many modifications, variations, and changes in detail can be made to the described embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A bowler performance tracking system monitors number of steps in an approach, a maximum rearward angle attained by a bowling ball during the approach, a release angle of the bowling ball upon release by a bowler onto a bowling lane, a ball speed, a ball trajectory, a frame score and a game score during a bowling game, said system comprising:
    a wearable performance tracking device dimensioned and configured to be worn by the bowler;
    said wearable performance tracking device comprises a housing assembly having a motion sensor camera unit mounted therein;
    a digital display assembly disposed on said housing assembly and visible to the bowler;
    a control assembly disposed in said housing assembly having a data storage unit configured to store an amount of data thereon, and
    said control assembly having a display interface operable with said digital display assembly to cause the number of steps, the maximum rearward angle, the release angle, the ball speed, the ball trajectory, the frame score, the game score, and a time of day to be displayed thereon.

2. The system as recited in claim 1, wherein said wearable performance tracking device comprises an adjustable mounting unit to removably attach said wearable performance tracking device to the bowler.

3. The system as recited in claim 1, wherein said housing assembly further comprises at least one data transfer port to transfer of said amount of data to or from said wearable performance tracking device via a physical connection.

4. The system as recited in claim 1, wherein said housing assembly further comprises at least one memory card port to transfer said amount of data to or from said wearable performance tracking device via a removable data memory card.

5. The system as recited in claim 1, wherein said housing assembly comprises a face disposed on one surface thereof.

6. The system as recited in claim 5, wherein said digital display assembly is at least partially disposed on said face of said housing assembly.

7. The system as recited in claim 1, wherein said display interface is operable with said digital display assembly to display a data access button.

8. The system as recited in claim 1, wherein said display interface is operable with said digital display assembly to display a data transfer button.

9. The system as recited in claim 1, wherein said display interface is operable with said digital display assembly to display a power control button.

10. The system as recited in claim 1, wherein said display interface is operable with said digital display assembly to display a wireless control button.

11. The system as recited in claim 1, wherein said display interface is operable with said digital display assembly to display a volume control button.

* * * * *